(12) United States Patent
Park

(10) Patent No.: US 7,049,285 B2
(45) Date of Patent: May 23, 2006

(54) BIOCOMPATIBLE POLYMERS INCLUDING PEPTIDE SPACER

(76) Inventor: Myung-Ok Park, #107-1403 Hakyul chunggu Apt., Hagye-dong, Nowon-gu, 139-230 Seoul (KR)

( * ) Notice: Subject to any disclaimer, the term of this patent is extended or adjusted under 35 U.S.C. 154(b) by 159 days.

(21) Appl. No.: 10/380,498

(22) PCT Filed: Oct. 31, 2002

(86) PCT No.: PCT/KR02/02036

§ 371 (c)(1), (2), (4) Date: Mar. 14, 2003

(87) PCT Pub. No.: WO03/037915

PCT Pub. Date: May 8, 2003

(65) Prior Publication Data

US 2003/0185798 A1 Oct. 2, 2003

(30) Foreign Application Priority Data

Oct. 31, 2001 (KR) ............................ 2001-0067369

(51) Int. Cl.
*A01N 37/18* (2006.01)
*A61K 38/00* (2006.01)

(52) U.S. Cl. ........................................................ 514/2
(58) Field of Classification Search ................ 424/85.4; 530/351; 525/54.1; 514/2
See application file for complete search history.

(56) References Cited

U.S. PATENT DOCUMENTS

| 4,179,337 | A | | 12/1979 | Davis et al. |
| 5,919,455 | A | * | 7/1999 | Greenwald et al. ...... 424/178.1 |
| 6,042,822 | A | * | 3/2000 | Gilbert et al. ............. 424/85.7 |
| 6,106,828 | A | | 8/2000 | Bisgard-Frantzen et al. |
| 6,251,866 | B1 | * | 6/2001 | Prakash et al. ............... 514/17 |
| 6,303,752 | B1 | | 10/2001 | Olsen et al. |
| 2004/0105839 | A1 | * | 6/2004 | Park ......................... 424/78.17 |
| 2004/0192769 | A1 | * | 9/2004 | Greenwald et al. ......... 514/483 |

FOREIGN PATENT DOCUMENTS

WO    WO 02/09766    * 2/2002

OTHER PUBLICATIONS

STN search results. pp. 131-146.*
Molineux. Pegylation: Engineering Improved Biopharmaceuticals for Oncology. vol. 23. No. 8 Pt 2, pp. 3S-8S.*
Pechar et al. Synthesis of (polyethylene glycol) block copolymers as potential water-soluble drug carriers. Collect Czech Chem Commun 1995. vol. 60, pp. 1765-1780.*
http://www.ilpi.com/msds/ref/aliphatic.html, pp. 1-2.*
Suzawa, T. et al, "Synthesis and HPLC Analysis of Enzymatically Cleavable Linker Consisting of Poly(ethylene glycol) and Dipeptide for the Development of Immunoconjugate", J. Control Release, Oct. 3, 2000, 69(1): 27-41, Abstract Only.
Francis Ge et al, "PEGylation of Cytokines and other Therapeutic Proteins and Peptides: The Importance of Biological Optimisation of Coupling Techniques", Intl J Hematol, Jul. 1998, 68(1):1-18 Abstract Only.

* cited by examiner

*Primary Examiner*—Christopher R Tate
*Assistant Examiner*—Marcela M Cordero Garcia
(74) *Attorney, Agent, or Firm*—Rodman & Rodman

(57) ABSTRACT

The present invention relates to new biocompatible polymer derivatives including peptide spacers of formula (I) and their methods of preparation. The present invention also relates to the conjugates formed by covalent or non-covalent bonding and their methods of preparation. These biocompatible polymers with peptide spacers providing regions of hydrophobicity and positive charge can enhance their interaction with cell membrane to increase the cell trafficking, endosomal disruption, the circulation half-life in blood, and the stability of conjugated therapeutic drug.

7 Claims, 2 Drawing Sheets

BIOCOMPATIBLE POLYMERS INCLUDING PEPTIDE SPACER

This patent application claims a benefit of priority from Korean Patent Application No. 2001-0067369 filed Oct. 31, 2001, through PCT Application Serial No. PCT/KR02/02036 filed Oct. 31, 2002, the contents of each of which is incorporated herein by reference.

FIELD OF THE INVENTION

The present invention relates to novel biocompatible polymer derivatives including peptide spacers and their methods of preparation. The present invention also relates to the bioconjugates of activated biocompatible polymers and biologically active molecules conjugated/bonded by covalent or non-covalent bonding.

BACKGROUND OF THE INVENTION

In the last decade, enormous progress in recombinant DNA technology has enabled the discovery and/or production of a large number of physiologically active proteins, peptides, enzymes, and genes, many of them having unforeseen potential to be used as pharmaceuticals.

Use of these proteins and peptides as medicines, however, suffers from many problems. First, peptides or proteins are very low in vivo absorption efficiency because they are easily hydrolyzed or degraded by enzymes within a short period of time after being taken into the body. Further, many pharmaceutically relevant peptides and proteins, even those having human primary structure, can be immunogenic, giving rise to production of neutralizing antibodies circulating in the blood stream. In addition, the clearance attributable to the reticuloendothelial system (RES) is high. Therefore, most protein and peptide drugs have been administered by injection, thus far. The administration by injection, however, causes the patients the pain and is accompanied by dangers. On the other hand, research in gene therapy has demonstrated potential for treatment of both acquired and inherited diseases. One of the major challenges for gene therapy is systemic delivery of a nucleic acid directly into an affected tissue. This requires development of a vehicle that is able to protect a nucleic acid from degradation, while delivering the genes of interest to specific tissues and target cell compartments. Non-viral gene delivery systems such as liposomes (H. M. Temin, J. Human Gene Therapy 111, 1990) or poly-L-lysine (PLL) (G. Y. Wu et al. 263 J. Biol. Chem. 14621, 1988) have drawbacks of low transfection efficiency or causing precipitation. Synthetic delivery systems also elicit fewer immunological complications with large scale repeated use (P. L. Felgner, 5 Adv. Drug Deliv. 163, 1990).

Conjugation of biologically active molecules, for example proteins or peptides, to synthetic macromolecules may afford great advantages when they are applied in vivo and in vitro. When being covalently bonded to macromolecules, biologically active molecules may exhibit modified surface properties and solubility, and thus may be increased in solubility within water or organic solvents. Further, the presence of macromolecules may make the conjugated proteins and peptides more stable in vivo as well as reduce the clearance by the intestines, the kidneys, the spleen, and/or the liver.

There have been many patents or publications regarding conjugation of biologically active molecules with polyethylene glycol (hereinafter, referred to as "PEG") or similar water soluble polyalkylene oxides (hereinafter, referred to as "PAO").

U.S. Pat. No. 4,179,337 discloses conjugates of biologically active polypeptides and PEG or polypropylene glycol (PPG) with a molecular weight of 500–20,000, which are water-soluble, biocompatible, biologically active, and non-immunogenic polymers. This patent discloses that the conjugation of PEG to proteins or peptides is achieved by reacting activated PEG to amino residues of proteins or peptides, lysine residues and N-termini. As for PEG activation, one of the hydroxyl groups of PEG is substituted with a methyl ether group while the other hydroxy group is bonded to an electrophilic functional group. Also it is described that PEG or PPG protects biologically active polypeptides from inactivation/denaturation.

U.S. Pat. No. 4,301,144 discloses the hemoglobin modified by conjugating hemoglobin with polyalkylene glycol or its derivatives. It is described therein that hemoglobin is increased in oxygen carrying potential and retention time in the body when being associated with PEG or water-soluble polymers.

Various proteins are reported to show extended half-lives and reduced immunogenicity in plasma when being conjugated with PEG (Abuchowski et al., Cancer Biochem. Biophys., 7, 175–186, 1984).

U.S. Pat. No. 5,951,974 and Algranati et al (Hepatology, 40 (suppl), 190A, 1999) describe that PEGylation of alpha interferon with PEG12000 as well as PEG40000 decreases the clearance rate, to achieve once-weekly subcutaneous injection instead of 3 times a week injection for native interferon.

Davis et al (Lancet, 2, 281–283, 1981) demonstrated that uricase-PEG conjugates had higher in vivo half-life and showed reduced side effects during the metabolism of uric acid.

Also, Niven et al (J. of Contr., Rel. 32, 177–189, 1994) demonstrated PEG conjugation of recombinant human granulocyte-colony stimulating factor (hereinafter, referred to as rhG-CSF) showed a more intense and extended white blood cell response relative to rhG-CSF alone.

However, there is a barrier to conjugating a number of linear polymers to proteins or peptides with retaining biological activity, because the active sites of proteins or peptides are spatially hindered. The conjugation of linear polymers with a molecular weight of 20,000 and higher has been attempted and resulted in the extended circulating half-life. The yield of this conjugate was, however, found to be very low and considered not to be economical.

To overcome the problem of conjugating linear polymer to proteins or peptides as mentioned above, the use of branched PEG has been attempted. U.S. Pat. No. 5,932,462 and U.S. Pat. No. 5,643,575 disclosed a branched or multi-armed aliphatic polymer derivative that is monofunctional and hydrolytically stable. The polymer arms are capped with relatively nonreactive end groups. The derivative can include a single reactive site that is located among the polymer moieties. However, these branched polymers with short length of linker between polymer and protein experience steric hindrance and thus reduce the reactivity and yield of product.

Also, U.S. Pat. No. 5,919,455 disclosed a branched aliphatic polymer derivative with various lengths of linkers including from 1 to 18 units of polyethylene glycol to improve the reactivity between polymer and protein. However, these branched PEG derivatives with a long linker including a PEG chain are too hydrophilic to use as efficient carriers for protein or genes.

Veronese et al. (Veronese, et al., Bioconjugate Chem, 12, 62, 2001) and WO 00/33881 introduced the preparation of branched PEGs with dipeptide as reporter to analyze the polymers easily and they showed different structures of polymers from the present invention.

SUMMARY OF INVENTION

Therefore, novel polymers are still required to deliver the biologically active peptides efficiently in vivo. The present inventor succeeded in preparing new polymers with peptide spacers to increase targeting of drugs and specific cell uptake resulting in increase of efficacy of drugs.

The present invention provides novel biocompatible polymers comprising peptide spacers.

The present invention also provides methods for producing the above novel biocompatible polymers comprising peptide spacers.

The present invention also provides novel activated biocompatible polymers comprising peptide spacers.

The present invention also provides methods for producing the above novel activated biocompatible polymer comprising peptide spacers.

Also, the present invention provides biologically active conjugates between the above novel activated biocompatible polymer and biologically active molecules conjugated/linked by covalent or non-covalent bonding.

Also, the present invention provides methods for producing the above conjugates.

Also, the present invention provides pharmaceutical compositions comprising the above conjugates.

DETAILED DESCRIPTION OF THE INVENTION

Figure 1:
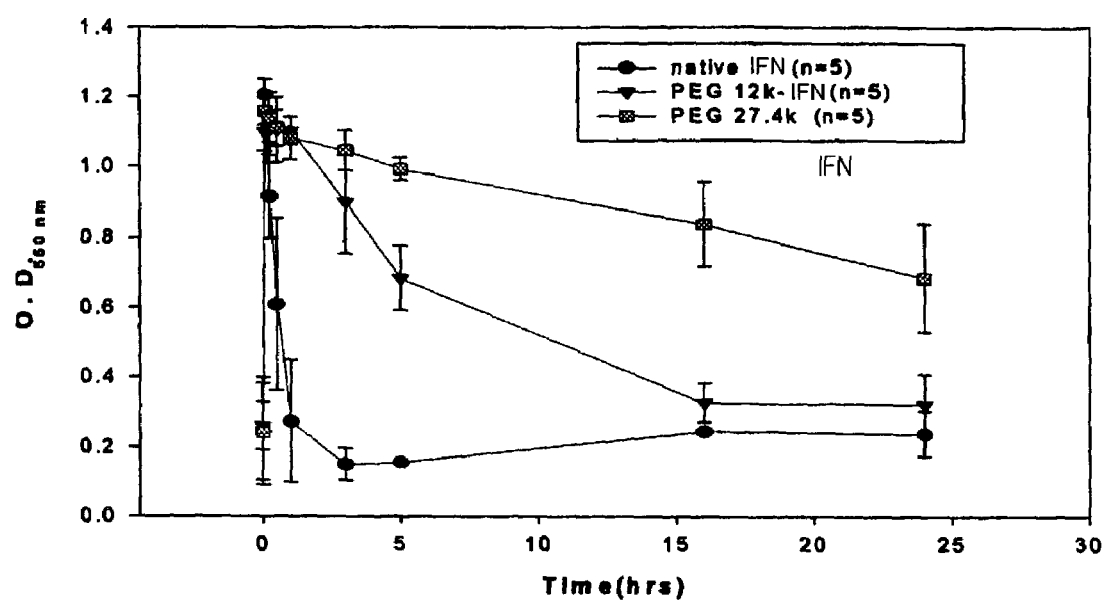
FIG. 1 shows the efficacy of biologically active conjugate (mPEG12000-OCH$_2$COGly-Gly)$_2$(2,4-diaminobutyric acid)-PEG'-interferon in rats.

The activated biocompatible polymer derivatives comprising peptide spacers according to the present invention are represented by the formula (I):

[P—OCH$_2$CO—(Y)]$_n$-(L)$_s$-(Q)$_t$-(Y')$_k$-A    (I)

wherein
P and Q may be the same or different and independently represent a biocompatible polymer;
t is an integer of 0 or 1,
Y and Y' may be the same or different and independently represent a peptide consisting of from 2 to 18 amino acid residues;
k is an integer of 0 or 1;
L represents an aliphatic linking moiety or diaminocarboxylic acid;
s is an integer of 0 or 1;
A represents a reactive functional group; and
n is an integer of 1 or 2.

Biocompatible Polymers, P or Q in Formula (I)
The polymers to be used in this invention have to be readily soluble in a wide range of solvents and biocompat-ible and non-immunogenic. The polymers of the present invention have a molecular weight of between about 300 and 100,000 daltons and preferably between about 2,000 and 20,000 daltons.

The biocompatible polymers (P or Q) of the present invention include but are not limited to polyethylene glycol (PEG), polypropylene glycol (PPG), polyoxyethylene (POE), polytrimethylene glycol, polylactic acid and its derivatives, polyacrylic acid and its derivatives, polyamino acid, polyoxazolidine, polyurethane, polyphosphazene, poly (L-lysine), polyalkylene oxide (PAO), polysaccharide, dextran, polyvinyl pyrrolidone, polyvinyl alcohol (PVA), polyacrylamide and other non-immunogenic polymers.

In another embodiment of the present invention, biocompatible polymers (P and Q) are a branched polymer, which can lead to form second and third branches from the biologically active molecules. In addition, bifunctional and hetero-bifunctional activated polymer esters can be used as the biocompatible polymer according to the present invention. The polymer used in the present invention can also be copolymerized with a bifunctional material, for example poly(alkylene glycol) diamine, to form a useful interpermeable network for permeable contact lenses, wound dressing, drug delivery system, etc.

Peptides, Y and Y' in Formula (I)

Amino acids for comprising the peptides designated as Y and Y' in Formula (I) include glycine, alanine, valine, leucine, isoleucine, methionine, proline, phenylalanine, tryptophan, serine, threonine, glutamine, tyrosine, cysteine, lysine, arginine, asparagine, histidine, glutamic acid and aspartic acid. In addition, β-alanine, oxy-proline, aminobutyric acid, ornithine, citrulline, homo-serine, diiodo tyrosine, triiodo tyrosine, deoxy-phenylalanine can be included. Also, both of D- and L-isomers can be included in the peptides according to the present invention as well, because the amino acids have optical isomers, except for glycine.

Linker, L in Formula (I): Aliphatic Linking Moiety

The aliphatic linking moiety (L) in Formula (I) is used to conjugate up to four activated biocompatible polymers (P and Q) to biologically active molecules by nucleophilic reaction. The suitable aliphatic linking moiety (L) can be substituted alkyl diamine or triamine, lysine ester and maleic acid ester derivatives, although it is not limited to these examples. It is preferable that the aliphatic linking moieties are not planar, to make the polymer less rigid.

The preferable embodiment of the present invention includes a multi-armed alkyl linking moiety (L) having 18 carbons. More preferably, the number of carbons is between 1 and 10. The alkyl group can also include hetero compounds such as nitrogen, oxygen or sulfur.

Linking moiety (L): Diaminocarboxylic Acid Moiety

Diaminocarboxylic acid linking moiety (L) in Formula (I) is used to conjugate up to four the activated biocompatible polymers (P and Q) to biologically active molecules by nucleophilic reaction. The formula is as follows:

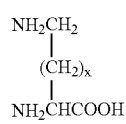

wherein x is an integer between 0 and 5.

The alkyl group can also include heterocompounds such as nitrogen, oxygen, or sulfur and be branched at carbon and nitrogen atoms thereof.

Functional Group, A in Formula (I)

The functional group (A) in the formula (I) is the activated group or moiety for linking to the biologically active molecules. To conjugate the biologically active molecules to biocompatible polymers, one of the end groups is converted into a reactive functional group which allows conjugation. This process is referred to as "activation" and the product is called an "activated" polymer. For instance, to conjugate poly(alkylene oxides) to biologically active molecules, one of the polymer hydroxyl end groups is converted into a reactive functional group such as carbonate and the product is called an activated poly(alkylene oxide).

The reactive functional group (A) of the formula I can be selected from the group consisting of (i) functional groups capable of reacting with an amino group, for example, (a) carbonates such as p-nitrophenyl and succinimidyl, (b) carbonyl imidazole, (c) azlactones, (d) cyclic imide thiones or (e) isocyanates or isothiocyanates, (ii) functional groups capable of reacting with carboxylic acid groups and reactive carbonyl groups, for example, (a) primary amines or (b) hydrazine and hydrazide functional groups such as acyl hydrazides, carbazates, semicarbazates and thiocarbazates; (iii) functional groups capable of reacting with mercapto or sulfhydryl groups, for example, phenyl glyoxals (see U.S. Pat. No. 5,093,531); (iv) functional groups capable of reacting with hydroxyl groups, for example, carboxylic acid, and (v) other nucleophiles capable of reacting with an electrophilic center.

A preferred reactive functional group (A) of the present invention includes but is not limited to N-hydroxysuccinimide ester (NHS), hydrazine hydrate ($NH_2NH_2$), carbonyl imidazole, nitrophenyl, isocyanate, sulfonyl chloride, aldehyde, glyoxal, epoxide, carbonate, cyanuric halide, dithiocarbonate, tosylate and maleimide.

Preferred Embodiment of Present Invention

One embodiment of activated biocompatible polymers of this invention includes activated linear polymer shown in the formula (Ia):

P—OCH$_2$CO—Y-A    (Ia)

wherein P, Y and A are the same as defined above.

The representative polymer of the formula (Ia) includes but is not limited to the polymers having the following formulae:

P—OCH$_2$CO—Y—NHS;

P—OCH$_2$CO—Y—NH$_2$NH$_2$; or

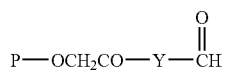

wherein P and Y are the same as defined above.

Another preferred embodiment of present invention provides the branched polymer including a carboxyl end group useful to make a prodrug having an ester group. This branched polymer can be represented by the formula (Ib):

[P—OCH$_2$CO—Y]$_n$-L-COOH    (Ib)

wherein P, n, L, and Y are the same as defined above.

Preferred polymer of the formula (Ib) includes but is not limited to the polymers having the following formulae:

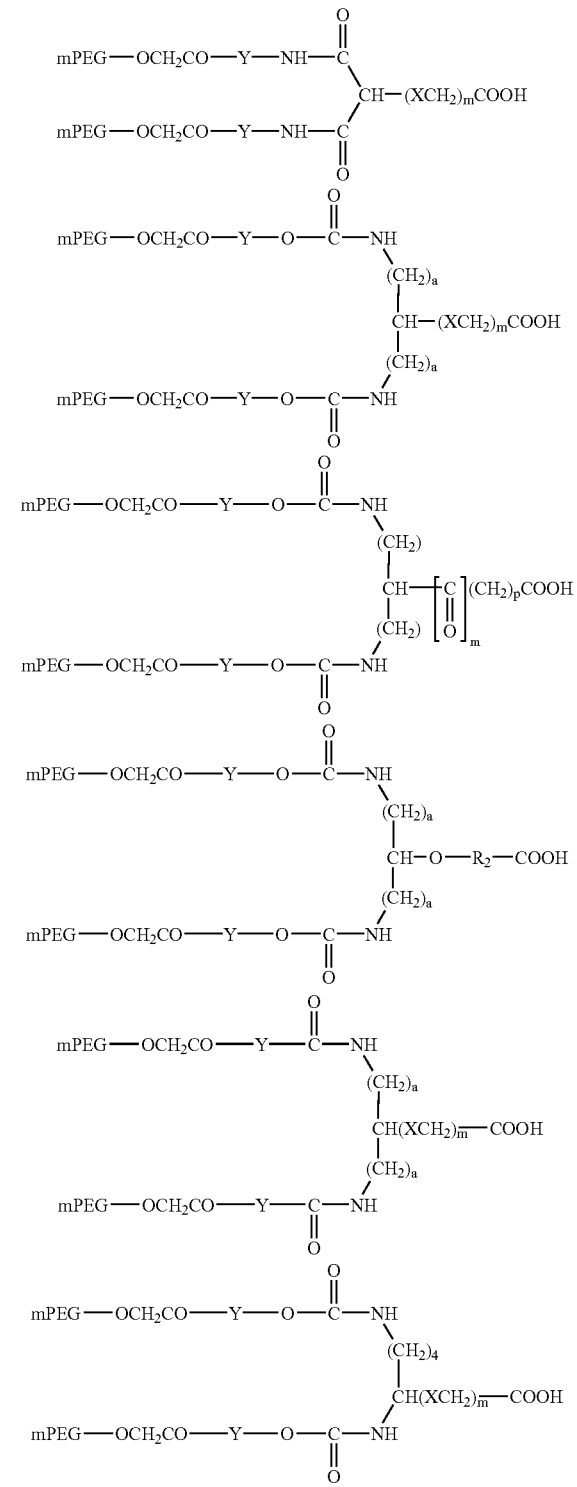

wherein

Y represents the peptide as defined above;

a is an integer between 1 and 5;

m is an integer between 0 and 1;

X represents O, NQ (wherein, Q is H, $C_{1-8}$ alkyl, $C_{1-8}$ branched alkyl, $C_{1-8}$ substituted alkyl, aryl or aralkyl), S, SO or $SO_2$;

p is an integer between 0 and 6; and $R_2$ is selected from the group consisting of —CO—NH—$(CH_2—)_dX_2$, —CO—NH—$(CH_2—CH_2—O—)_dX_2$,

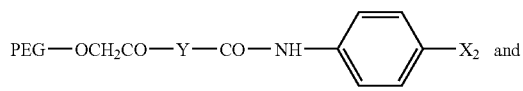

and

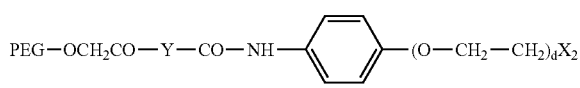

in which d is an integer between 1 and 18, and $X_2$ represents H, OH, $NH_2$ or COOH. The PEG is presented as an example and it would be understood by those skilled in the art that PEG can be substituted by other polyalkylene oxides or other biocompatible polymers.

Another further embodiment of the present invention provides branched polymers having the following formulae:

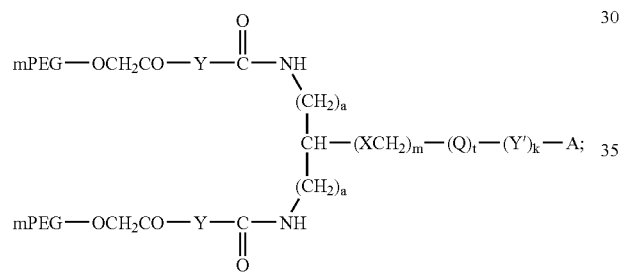

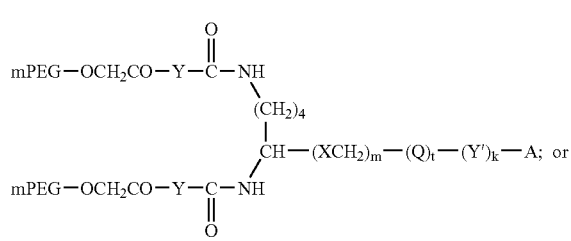

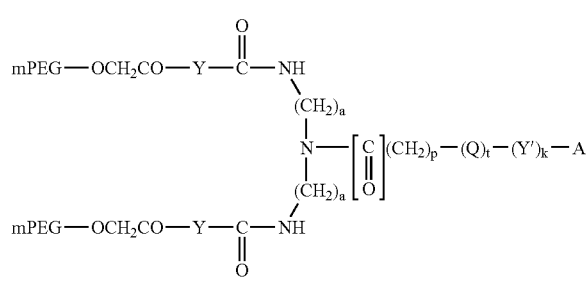

wherein Y, Y', Q, t, k, A, a, m, p and x are the same as defined above.

A still further embodiment of present invention provides branched polymers shown in the formula (Ic):

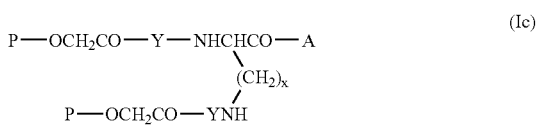
(Ic)

wherein P, Y and A are the same as defined above and x is an integer between 0 and 5.

The branched polymers in the formula (Ic) include but are not limited to the polymers having the following formulae:

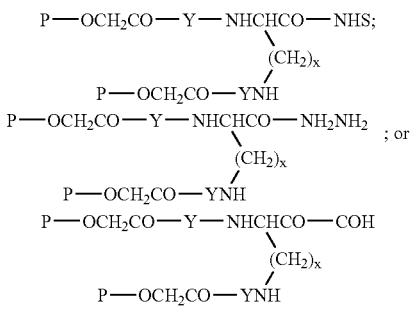

wherein P, Y and x are the same as defined above.

Another further preferred embodiment provides branched polymers represented by the formula (Id):

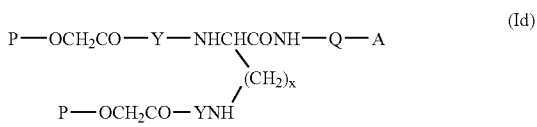
(Id)

wherein P, Y, Q, A and x is same as specified above.

The branched polymers of formula (Id) include but are not limited to the polymers having the following formulae:

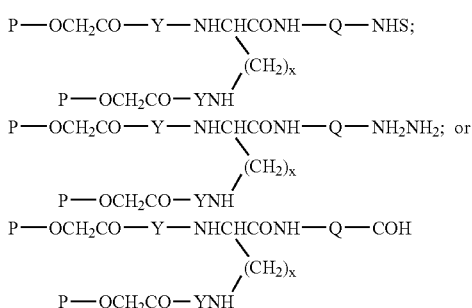

wherein, P, Y, Q, and x are the same as defined above.

Preparation of Biocompatible Polymers of the Formula (I)

A process for producing biocompatible polymers of the formula (I) includes the following steps of (a) synthesizing P—$OCH_2$COOH from P—OH by esterification;

(b) activating P—OCH$_2$COOH and reacting the resulting activated P—OCH$_2$COOH with peptide (Y) to produce P—OCH$_2$CO—Y—COOH;

(d) activating P—OCH$_2$CO—Y—COOH and reacting the resulting activated P—OCH$_2$CO—Y—COOH with an aliphatic linking moiety having a nucleophile to produce [P—OCH$_2$CO—Y]$_n$-L;

(e) reacting the resulting [P—OCH$_2$CO—Y]$_n$-L with activated polymer (Q) to produce [P—OCH$_2$CO—Y]$_n$-(L)$_s$-(Q)$_t$;

(f) reacting the resulting [P—OCH$_2$CO—Y]$_n$-(L)$_s$-(Q)$_t$ with peptide (Y') to produce [P—OCH$_2$CO—Y]$_n$-(L)$_s$-(Q)$_t$-(Y'); and then (g) activating [P—OCH$_2$CO—Y]$_n$-(L)$_s$-(Q)$_t$-(Y') to obtain activated polymer having the formula (I).

One method to activate polymers is to react p-nitrophenyl chloroformate with hydroxyl groups of polymers to produce activated p-nitrophenyl carbonated polymers which can be reacted with biologically active molecules. Also, p-nitrophenyl carbonated polymers can act as intermediates. p-Nitrophenyl carbonated polymers can be reacted with excess of N-hydroxysuccinimide to produce activated succinimidyl carbonated polymers. Alternatively, p-nitrophenyl carbonated polymers can be reacted with anhydrous hydrazine to produce carbazate polymers.

Another method to activate the polymers is as follows: Polymers are reacted with alkyl haloacetate under basic conditions to yield alkyl ester as an intermediate and this intermediate is reacted with trifluoroacetic acid to produce polymers having a carboxyl end group. In this reaction, the ratio of alkyl acetate to polymer is above 1:1. The second step of reacting alkyl ester with acid is carried out at between 0° C. and 50° C., preferably between 20° C. and 30° C. Also, the second step can be performed in an aqueous system. Preferably, the alkyl acetate used is a tertiary alkyl haloacetate represented as follows:

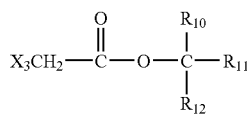

wherein, X$_3$ is Cl, Br or I, R$_{10}$, R$_{11}$ and R$_{12}$ are independently selected from the group consisting of C$_{1-8}$ alkyl, C$_{1-8}$ substituted alkyl and C$_{1-8}$ branched alkyl and aryl group. Preferred tertiary haloacetate includes tertiary butyl haloacetate such as t-butyl bromoacetate and t-butyl chloroacetate. Suitable bases include potassium butoxide, butyl lithium, sodium amide, and sodium hydroxide. Suitable acids include trifluoroacetic acid, sulfuric acid, phosphoric acid and hydrochloric acid.

Polymers having an amino end group can be reacted with hydroxylic acid such as lactic acid and glycolic acid to produce hydroxyl amide and then can be activated by reacting with p-nitrophenyl chloroformate.

As one embodiment, mPEG-OH is dissolved in THF under nitrogen atmosphere and stirred at room temperature with adding Na and naphthalene solution and then bromoethylene acetate is added. After 3 hr reaction, product is precipitated in cold ether, filtered, and washed with ether and dried under vacuum. The product, mPEG-OCH$_2$COOH, is dissolved in methylene chloride (hereinafter, referred to as MC) and reacted with NHS and dicyclohexyl carbodiimide (hereinafter, referred to as DCC) to produce mPEG-OCH$_2$COONHS.

Consequently, peptides (Y) such as Ala-His or Gly-Gly-ethyl ester, Gly-His, His-His, Lys-Lys or other peptides are dissolved in borate buffer solution with stirring and mPEG-OCH$_2$COONHS is added. After 48 hr reaction at room temperature, pH is adjusted by adding oxalic acid, extracted in MC, and the product, mPEG-OCH$_2$COYCOOH, is dried under vacuum.

Also, mPEG-OH is dissolved in toluene and evaporated to dryness and then dissolved in MC and reacted overnight with p-nitrophenyl chloroformate at room temperature with stirring where pH is adjusted to 8 with triethyl amine (hereinafter referred to TEA). The product is precipitated in ether, filtered, and dried. Peptide(Y) is added to this product, PEG-nitrophenyl carbonate, to produce PEG-Y—COOH.

The activated ester is converted to ester of carboxyl group derived from acidic alcohol such as 0- and p-nitrophenyl, 2,4-dinitrophenyl, N-hydroxy succinimide, 2- and 4-thiopyridine, 8-hydroxy quinoline, and 1-hydroxy benzotriazole (U.S. Pat. No. 4,101,380). mPEG-OCH$_2$CO—Y—NHS can be prepared in accordance with the same manner as described above.

Also, mPEG-OCH$_2$CO—Y—NHNH$_2$ is prepared as follows. mPEG-OCH$_2$CO—Y—COOH is dissolved in MC, SOCl$_2$ is added to reflux for 3 hrs, then the reaction is cooled to room temperature to evaporate to dryness. Yielded powder, mPEG-OCH$_2$CO—Y—COCl, is dissolved in MC and NH$_2$NH$_2$ is added. The mixture is purified on a silica column and evaporated to dryness.

Also, mPEG-OH is dissolved in dioxane or benzene and K$_2$CO$_3$ is added to prepare mPEG-OCH$_2$CO—Y—COH. Then, 1 to 5 moles of catalyst is added and bubbled with air or oxygen at 40° C. The product is precipitated in ether, filtered, and dried under vacuum.

PEG-hydrazine or PEG-NHNH$_2$ can be prepared by reacting PEG-aldehyde in DMSO with excess hydrazine and reducing agents such as NaBH$_3$CH$_3$ or NaBH$_4$.

To synthesize the branched PEG polymers, PEG-Y—NHS obtained as described above, is dissolved in buffer solution at pH 8–9 and lysine is added and the reaction mixture is stirred for 30 minutes at room temperature. The product is purified by size exclusion chromatography and concentrated for further precipitation in ether. PEG-Y-nitropheny carbonate can thus be obtained instead of PEG-Y—NHS.

Another method to prepare branched PEG derivatives of the present invention includes direct synthesis by reacting mPEG-nitrophenyl with NH$_2$AlaHisCOOH in aqueous solution. This method has an advantage of reducing the numbers of steps in synthetic process over other methods.

As to the method for inserting PEG' linker to the branched PEG derivatives

1) A heterobifuntional PEG is synthesized as follows (Makromol Chem. 184, 1849–1859, 1983). Amino groups of 3-amino methyl-3,5,5-trimethyl cyclohexanol are protected by succinic anhydride. Equivalent moles of potassium dihydronaphthylide are added to THF solution to make potassium alcoholate. Then, oxirane is polymerized in benzene/THF at 50° C. under vacuum. Imido terminal PO (polyoxirane) is hydrolyzed at 25° C. by adding KOH solution and extracted by chloroform to obtain the final product in hexane.

Another method as described in U.S. Pat. No. 5,679,765 includes the reaction of epoxy compounds with polymerization initiator, potassium bis(trimethylsilyl)amide or phthalimide to make heterofunctional NH$_2$—(CH$_2$CH$_2$ O)$_n$—CH$_2$CH$_2$R$_2$ in which R$_2$ is mercapto, carboxyl or hydroxyl group and n is an integer between 5 and 10,000.

2) Heterobifunctional PEG derivatives prepared as described above and the branched PEG-NHS are dissolved in MC and reacted at 40° C. for 2 days. Then the reaction mixture is filtered by celite, washed with ether, and dried under vacuum. (mPEG-Y—)$_2$-Lys-PEG'-COOH obtained is activated to NHS.

Biologically Active Molecules for Coupling with Activated Biocompatible Polymers of the Formula (I)

In another aspect, the present invention provides the conjugates formed by coupling biologically active molecules with activated biocompatible polymers of the formula (I).

The terms "biologically active molecules" means all complexes of nucleophiles conjugated with activated biocompatible polymers, and which retain at least some of the biological activity. The terms "biologically activity" used herein is not limited by physiological or pharmacological activity. For example, Some complexes of nucleophiles containing enzymes have enhanced reaction rates in organic solvent. Similarly, some polymer conjugates including protein such as Con-canavalin A, or immunoglobulin can be used in diagnostics in the laboratory. In general, biologically active molecules can be naturally formed or chemically synthesized, and include proteins, peptides, polypeptides, enzymes, biomedicines, genes, plasmids or organic residues.

Polypeptides and peptides of interest include, but are not limited to, hemoglobin, serum proteins (for example, blood factors including Factors VII, VIII, and IX), immunoglobulins, cytokines (for example, interleukins), alpha-, beta- and gamma-interferons, colony stimulating factors including granulocyte colony stimulating factors, platelet derived growth factor (PDGF) and phospholipase-activating protein (PLAP). Other proteins of general biological or therapeutic interest include insulin, plant proteins (for example, lectins and ricins), tumor necrosis factors (TNF) and related alleles, growth factors (for example, tissue growth factors and epidermal growth factors), hormones (for example, follicle-stimulating hormone, thyroid-stimulating hormone, antidiuretic hormones, pigmentary hormones, parathyroid and progesterone-releasing hormone and derivatives thereof), calcitonin, calcitonin gene related peptide (CGRP), synthetic enkephalin, somatomedins, erythropoietin, hypothalamic releasing factors, prolactin, chorionic gonadotropin, tissue plasminogen activator, growth hormone releasing peptide (GHRP), thymic humoral factor (THF) and the like. Immunoglobulins of interest include IgG, IgE, IgM, IgA, IgD and fragments thereof.

Some proteins such as interleukin, interferon, and G-CSF can be produced in non-glycosylated form by DNA recombinant technology, which is also included in active substances in the present invention.

The protein or peptide of the present invention is not limited to the specific therapeutic agents but applied to the all substances having biological activity. Particularly, natural or synthetic drugs containing one or a few binding sites to polymers are suitable. For example, agents for chemotherapy include anti-cancer agents such as paclitaxel, taxotere, taxotere derivatives, camptothecine, photophilotoxy, atracycline, methotrexate, cardiovascular agents, gastrointestinal agents, central nervous system-activating agents, analgesics, fertility agents, contraceptive agents, anti-inflammatory agents, steroidal agents, vasodilating agents, and vasoconstricting agents.

The biologically active materials of the present invention also include any portion of a polypeptide demonstrating in vivo bioactivity. This includes amino acid sequences, antibody fragments, binding molecules including fusions of antibodies or fragments, polyclonal antibodies, monoclonal antibodies, catalytic antibodies and the like. Other proteins of interest are allergen proteins such as ragweed, Antigen E, honeybee venom, mite allergen, and the like.

Also, the present invention includes enzymes, such as carbohydrate-specific enzyme, proteolytic enzyme, oxidation-reduction enzyme, transferase, hydrolase, lyase, isomerase, and ligase. The enzymes of the present invention are not limited to the specific enzymes, they include asparaginase, arginase, arginine deiminase, adenosine deaminase, superoxide dismutase, endotoxinase, catalase, chymotrypsin, lipase, uricase, adenosine diphosphatase, tyrosinase, glucose oxidase, glucosidase, galactosidase, and glucouronidase.

The substances described above are examples for suitable coupling-nucleophiles with polymers. Other biologically active molecules with suitable nucleophiles are also included although they were not mentioned herein.

The present invention also includes antisense oligonucleotides, genes, and plasmid DNA. These nucleic acid molecules form complexes with polymers by non-covalent bonding, such as hydrophobic interaction.

The conjugates of the present invention are biologically active and can be applied to various therapeutic uses. The therapeutic compound conjugates with branched polymer derivatives of the present invention can be injected to mammals which need enzyme therapy, gene therapy, or blood factors.

Preparation of Conjugates

The method of preparing the conjugates of the present invention includes the reaction of biologically active nucleophilic substances retaining at least partial bioactivity with activated polymers under optimized conditions by physically mixing. One or more polymers can be conjugated to biologically active molecules. The conjugates can be expressed as the following formula:

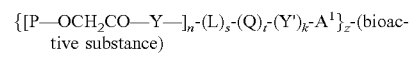

{[P—OCH$_2$CO—Y—]$_n$-(L)$_s$-(Q)$_t$-(Y')$_k$-A$^1$}$_z$-(bioactive substance)

wherein P, Y, n, L, s, Q, t, Y' and k are the same as defined above; A$^1$ is a linker between the biocompatible polymer and the bioactive substance; and z is the number of polymers attached to the bioactive substance and is between 1 and the number of binding sites of biologically active molecules. The extent of reaction can be stoichiometrically controlled by varying the amounts of reactants by well known methods. The conjugation of biologically active protein or peptide to one or more activated branched polymers can be performed by chemical reaction. For example, the molar ratio of protein-polymer, peptide-polymer, enzyme-polymer, antibody-polymer, drug-polymer conjugates is in the range of from 1:1 to 1:100 and preferably in the range of from about 1:1 to 1:20.

Similarly, the molar ratio of antisense oligonucleotide, gene, and plasmid DNA-polymer conjugates is in the range of from 1:1 to 1:100 and preferably in the range of from about 1:1 to 1:20.

The rate of conjugation reaction of biologically active protein or peptide with one or more activated branched polymers is dependent on the pH of buffer solution. In general, the pH of reaction buffer for protein and peptide conjugation is between 4 and 9, preferably between 6.5 and 8, more preferably at pH 7.4. The organic or small chemical compounds can be reacted in non-aqueous system. The suitable temperature for the conjugation reaction is in the range of 0 to 60° C. and preferably in the range of 4 to 30° C. Also, the reaction time of 5 minutes to 10 hours is preferable in this preparation. The conjugates prepared can be purified by diafiltration, and/or column chromatography.

Pharmaceutical Composition

In another aspect of the present invention, there is provided a method for the treatment of various medical conditions in mammals, preferably humans, which comprises administering a biologically active non-antigenic conjugate to said subject. The biologically active materials for the biologically active non-antigenic conjugates can be selected properly according to the medical conditions to be treated. For example, where interferon is used as the biologically active material, the medical conditions to be treated include, but are not limited to, cell proliferative disease, especially cancer (for example, Kaposi's sarcoma, ovarian cancer and multiple myeloma) and viral infection (for example, herpes simplex, cytomegalovirus and Epstein-Barr virus).

The frequency of administration is dependent on the biologically active molecules and is well known by patient situation. In case of protein drug, the frequency of administration is generally once every other day, preferably once or twice a week. The route of administration includes i.v., i.m., s.c., intranasal, oral or other permitted systemic or local administration routes.

The conjugates of the present invention can also be administered with other carriers which are permitted pharmaceutically. The pharmaceutical formulation can be prepared by well known methods. The common carriers include adjuvants such as Tris-HCl, acetate, phosphate buffer solution, human serum albumin, diluents like polyoxyethylene sorbitol, preservatives and/or solubilizers such as thimerosol and benzyl alcohol. Also the pharmaceutical formulation containing the conjugates of the present invention can be solution, suspension, tablet, capsule, or freeze-dried powder.

The following examples further describe and demonstrate embodiments within the scope of the present invention. The examples are given solely for the purpose of illustration and are not to be construed as limitations of the present invention, as many variations thereof are possible without departing from the spirit and scope of the invention.

1. Preparation of Activated PEG Derivatives

EXAMPLE 1

Synthesis of mPEG5000-OCH$_2$COGly-GlyCOOH 3.8 g of mPEG-nitrophenyl (fw 5165.12, 0.75 mol, 1 eq, 5000 Da) was dissolved in 150 ml of methylene chloride (MC) and 0.71 ml of triethylamine (TEA, fw 101.19, 7.5 mmol, 10 eq, d=1.069) was added to the solution. The reaction mixture was then stirred at room temperature for 30 minutes. 0.297 g of NH$_2$GlyGlyCOOH(fw 132.12, 2.25 mmol, 3 eq, 0.297 g) was added dropwise to the mixture and stirred for another 2 hours. 0.916 g of 4-dimethylaminoethylaminopyridine (DMAP, fw 122.17, 7.5 mmol, 10 eq) was added and the reaction mixture was kept overnight.

After the completion of reaction, the pH of the reaction mixture was adjusted to 2 or 3 by adding 1N HCl and the product was extracted in 300 ml of H$_2$O and 100 ml of MC three times. The resulting extract was crystallized in a 2:1 solution of ether and isopropyl alcohol (IPA), filtered and dried under vacuum to afford 3.65 g (95.9% yield) of the title polymer as a white solid.

EXAMPLE 2

Synthesis of mPEG12000-OCH$_2$COGly-GlyCOOH 0.27 g of mPEG12000-OCH$_2$COGly-GlyCOOH (0.025 mmole) was synthesized by the same method as described in <Example 1> except that mPEG-nitrophenyl(12000) was used instead of mPEG-nitrophenyl(5000).

2. Preparation of Branched PEG Having PEG' Linker and Its Derivative

EXAMPLE 3

Synthesis of activated branch (mPEG5000-OCH$_2$COGlyGly)$_2$-Lys-NHS

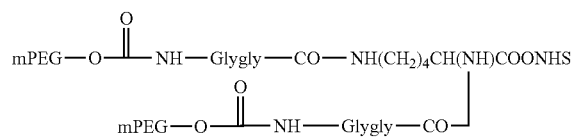

1.01 g of mPEGOCH$_2$CONHGlyGlyCOOH(fw 5174.17, 0.2 mmol, 2 eq) prepared in <Example 1> was dissolved in 10 ml of MC and reacted at RT for 30 minutes after adding 0.26 g of dicyclohexylcarbodiimide (DCC) (fw 266.33, 1 mmol, 5 eq). 0.018 g of NH$_2$(CH$_2$)$_4$CH(NH$_2$)COOH(lysine-.HCl, fw 182.6, 0.1 mmol, 1 eq) was added and stirred for another 2 hours and stored overnight after adding 0.122 g of 4-dimethylaminoethylaminopyridine (DMAP, fw 122.17, 1 mmol, 5 eq).

The reaction mixture was extracted in MC three times. After the completion of reaction, the pH of reaction mixture was adjusted by adding 1N HCl to 2 or 3 and the product was extracted in 150 ml H$_2$O and 80 ml of MC three times. The solid product (0.95 g, 92.7% yield) was crystallized in isopropyl alcohol (IPA), washed with ether after filtration, and dried under vacuum.

Then, 82.5 mg of mPEGOCH$_2$CONHGlyGlyCO)$_2$Ly-sCOOH(fw 10462.7, 0.008 mmol, 1 eq) was dissolved in 2 ml of MC and stirred for 30 minutes after addition of 0.009 g of DCC (fw 266.33, 10 eq, 0.08 mmol). 0.02 g of N-hydroxysuccinimide (NHS) (fw 115.09, 10 eq, 0.08 mmol) was then added and stirred for 48 hrs followed by filtration using celite prior to drying. The solid product was crystallized in IPA on ice bath, filtered, rinsed with ether, and dried under vacuum. 78 mg of white solid product was obtained (yield: 95.2%).

EXAMPLE 4

Synthesis of activated branch (mPEG12000-OCH$_2$COGly-Gly)$_2$Lys-NHS 25 mg of branched mPEG12000-OCH$_2$COGly-Gly)$_2$Lys-NHS was synthesized by the same method as described in <Example 3> except that 15 mg of mPEG12000-OCH$_2$COGly-GlyCOOH was used instead.

EXAMPLE 5

Synthesis of activated branch (mPEG5000-OCH₂COGly-Gly)₂Lys-PEG3400NHS with long linker

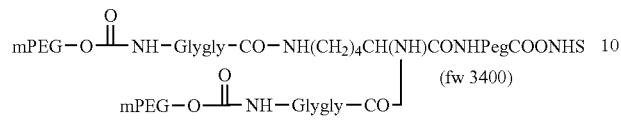

43.5 mg of (mPEG5000-OCH₂CONHGlyGlyCO)₂LysCOONHS(fw 10550, 1 eq, 0.0041 mmol) prepared in <Example 3> was dissolved in 2 ml of MC and added of 3.91 ul of TEA(fw 101.19, 10 eq, 0.041 mol). The reaction mixture was stirred for 30 minutes followed by addition of 41.8 mg of NH₂PEGCOOH(fw 3400, 2 eq, 0.0123 mmol). It was then stirred for another 2 hours and stored overnight after adding 0.122 g of DMAP(fw 122.17, 1 mmol, 5 eq).

After the completion of reaction, the pH of the reaction mixture was adjusted to 2 or 3 by adding 1N HCl and the product was extracted in 20 ml H₂O and 40 ml of MC. The white solid product (25 mg, 52.6% yield ) was crystallized in IPA, washed with ether after filtration, and dried under vacuum.

30 mg of (mPEG5000-OCH₂CONHGlyGlyCO)₂LysCONHPEGCOOH(fw 13844, 0.0022 mmol, 1 eq) was used according to the same method as described in <Example 1> to synthesize 25 mg of mPEG5000-OCH₂COGly-Gly)₂Lys-PEG3400-NHS.

EXAMPLE 6

Synthesis of activated branch (mPEG12000-OCH₂COGly-Gly)₂Lys-PEG3400NHS with long linker 0.05 g of (mPEG12000-OCH₂COGly-Gly)₂Lys-PEG3400NHS was synthesized by the same method as described in <Example 5> except that 60 mg of mPEG12000-OCH₂COGly-Gly)₂Lys-NHS prepared in <Example 4> was used instead.

EXAMPLE 7

Synthesis of activated branch (mPEG5000-OCH₂COGly-Gly)₂Lys-PEG3400NHNH₂

0.1 g of branched (mPEG5000-OCH₂COGly-Gly)₂Lys-PEG3400NHS (0.007 mmole) synthesized in <Example 5> was dissolved in MC and 0.05 g of SOCl₂(0.4 mmole) was added. After reflux for 3 hours, the reaction was cooled to RT followed by evaporation. 0.08 g of brown product mPEG5000-OCH₂COGly-Gly)₂Lys-PEG3400-COCl was obtained. mPEG5000-OCH₂COGly-Gly)₂ Lys-PEG3400-COCl (1.1 mmole) obtained above was dissolved in MC and NH₂NH₂, and H₂O 10 ml was added. The reaction mixture was stirred at RT for 3 hours and dried by evaporation. It was then purified on silica column and dried under vacuum. A yellow oil (1 mmole, 92% yield) was obtained.

EXAMPLE 8

Synthesis of activated branch (mPEG12000-OCH₂COGly-Gly)₂Lys-PEG3400NHNH₂

0.12 g of branched (mPEG12000-OCH₂COGly-Gly)₂Lys-PEG3400NHNH₂ was synthesized by the same method as described in <Example 7> except that 0.15 g of (mPEG12000-OCH₂COGly-Gly)₂Lys-PEG3400NHS (0.005 mmole) obtained in <Example 6> was used instead.

EXAMPLE 9

Synthesis of mPEG12000-OCH₂COAla-HisCOOH 1.23 g of mPEG12000-nitrophenyl(fw 12165.12, 0.1 mol, 1 eq)in 150 ml of MC and 0.095 ml of TEA (fw 101.19, 1 mmol, 10 eq, d=1.069) were stirred at RT for 30 minutes and 68 mg of NH₂AlaHisCOOH(fw 226.2, 0.3 mmol, 3 eq) was then added. The reaction mixture was stirred for another 2 hours and stored overnight after addition of 0.122 g of DMAP(fw 122.17, 1 mmol, 10 eq). After the completion of reaction, the pH of reaction mixture was adjusted to 2 or 3 by adding 1N HCl and the product was extracted in 50 ml H₂O and 20 ml of MC three times. The white solid product (1.15 g, 93.9% yield) was crystallized in IPA, washed with ether after filtration, and dried under vacuum.

EXAMPLE 10

Synthesis of activated branch (mPEG12000-OCH₂COAla-His)₂Lys-NHS 1.08 g of mPEG12000-OCH₂COAla-HisCOOH(fw 12252.2, 0.088 mmol, 2.2 eq) synthesized in <Example 9> was used according to the same method as described in <Example 3> to afford 0.95 g (yield: 97.1%) of (mPEG12000-OCH₂COAla-His)₂Lys-NHS as a white solid.

EXAMPLE 11

Synthesis activated branch (mPEG12000-OCH₂COAla-His)₂Lys-GlyNHS with amino acid linker

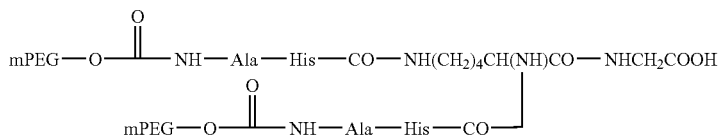

0.49 g of (mPEG12000-OCH₂CONHAlaHisCO)₂LysCOONHS(fw 24565.49, 1 eq) in 2 ml of MC and 0.016 ml of TEA (fw 101.19, 10 eq, 0.2 mol) were stirred at RT for 30 minutes. The reaction mixture was stirred for another 2 hours after adding 4.5 mg NH₂CH₂COOH (Glycine fw 75.07, 3 eq, 0.06 mmol) and 37 mg of DMAP (fw 122.17, 10 eq, 0.3 mmol) was then added to react overnight.

After the completion of reaction, the pH of reaction mixture was adjusted to 2 or 3 by adding 1N HCl and the product was extracted in 20 ml of H₂O and 20 ml of MC three times. The white solid product (0.42 g, 85.5% yield ) was crystallized in IPA, washed with ether after filtration, and dried under vacuum.

EXAMPLE 12

Synthesis of activated branch (mPEG12000-OCH₂COAla-His)₂-(2,4-diaminobutyric acid)-GlyNHS with amino acid linker mPEG12000-OCH₂COAla-HisCOOH (fw 12252.2, 0.088 mmol, 2.2 eq, 1.08 g) prepared in <Example 9> was used to synthesize title compound (mPEG12000-OCH₂COAla-His)₂-(2,4-diamonbutyric acid)-GlyNHS by the same method as described in <Example 3> except that 2,4-diaminobutyric acid was used instead of lysine.

EXAMPLE 13

Synthesis of activated branch (mPEG12000)₂-Ala-His-PEG3400-NHS with macromolecule linker A. Synthesis of (mPEG12000)₂-Ala-His-COOH

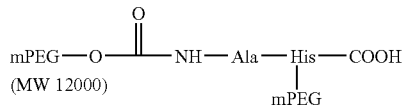

10 mg of NH₂-Ala-His-COOH(MW=226.2, 0.04 mmol, 1 eq) was dissolved in 20 ml of d-water and pH was kept at 8.0 for 3 hrs by adding 0.2 N NaOH. The reaction was carried out overnight after addition of mPEG-NPC (MW=12000, 0.125 mmol, 3 eq, 1.5 g). After the completion of reaction, the pH of reaction mixture was adjusted to 2 or 3 by adding 1N HCl and the product was extracted in 50 ml H₂O and 20 ml of MC three times. The white solid product (1.2 g, 80% yield) was evaporated, crystallized in IPA, washed with ether after filtration, and dried under vacuum.

B. Synthesis of (mPEG12000)₂-Ala-His-PEG3400-NHS (mPEG12000)₂-Ala-His-PEG3400-NHS was synthesized from (mPEG12000)₂-Ala-His-COOH by the methods as described in <Example 3> and <Example 5>.

EXAMPLE 14

Preparation of (mPEG12000-OCH₂CONH-Ala-His)₂(2,4-diaminobutyric acid)-Gly-campthothecin conjugates 0.1 g of (mPEG12000-OCH₂CONH-Ala-His)₂ (2,4-diaminobutyric acid)-Gly-COOH(0.004 mmoles) prepared in <Example 12>, 280 mg (0.8 mmoles) of campthothecin, 1 mg (0.008 mmoles) of diisopropylcarbodiimide (DIC) and 1 mg (0.008 mmoles) of DMAP were added to 2 ml of MC at 0° C. The mixture was heated to RT and stirred for 18 hrs and dried by rotary evaporation. The product was recrystallized in IPA to yield 34 mg.

EXAMPLE 15

Preparation of (mPEG12000-OCH₂CO-Gly-Gly)₂(2, 4-diaminobutyric acid)-Gly-paclitaxel conjugates 0.1 g of (mPEG12000-OCH₂CO-Gly-Gly)₂ (2,4-diaminobutyric acid)-Gly-COOH (0.004 mmoles) prepared according to the procedures of <Example 4> and <Example 12>, 2.8 mg (0.8 mmoles) of paclitaxel, 1 mg (0.008 mmoles) of DIC and 1 mg (0.008 mmoles) of DMAP were added to 1 ml of MC at 0° C. The mixture was heated to RT and stirred for 18 hrs and dried by rotary evaporation. The product was recrystallized in IPA to yield 34 mg of the title conjugate.

EXAMPLE 16

Preparation of (mPEG12000-OCH₂COGly-Gly)₂(2, 4-diaminobutyric acid)-PEG'-interferon conjugate 1 mg of interferon dialyzed into 0.1 M phosphate buffer solution, pH 7.0 was reacted with 7.4 mg of (mPEG12000-OCH₂COGly-Gly)₂(2,4-diaminobutyric acid)-PEG'-NHS at RT for 1 hr. After the reaction was complete, (mPEG12000-OCH₂COGly-Gly)₂(2,4-diaminobutyric acid)-PEG'-IFN was purified by size exclusion chromatography.

EXAMPLE 17

Preparation of (mPEG12000-OCH₂COGly-Gly)₂(2, 4-diaminobutyric acid)-PEG'-G-CSF conjugates 1 mg of G-CSGF dialyzed into 0.1 M phosphate buffer solution, pH 7.5 was reacted with 7.5 mg of (mPEG12000-OCH₂COGly-Gly)₂(2,4-diaminobutyric acid)-PEG'-NHS at RT for 1 hr. After the reaction was complete, (mPEG12000-OCH₂COGly-Gly)₂(2,4-diaminobutyric acid)-PEG'-G-CSF was purified by size exclusion chromatography.

EXAMPLE 18

Measurement of efficacy of (mPEG12000-OCH₂COGly-Gly)₂(2,4-diaminobutyric acid)-PEG'-IFN in rats MDBK cells counted in a conc. of 7.5×10⁵ cells/ml were treated in 5% FBS/MEM media. 100 ul of cell solution was put in each well of 96 well plates and added with 100 ul of serum from PEG-IFN <Example 16> injected in rats, and incubated in a CO₂ incubator for 20 hours. 100-fold diluted virus (100 ul) was added and incubation continued for another 20 hours. The virus media in each well was removed, and 50 ul of 0.05% crystal violet dye solution was added to each well. The absorbance at 550 nm was read by a Microplate reader to measure the activity of IFN. The results are presented in FIG. 1.

EXAMPLE 19

Figure 2:
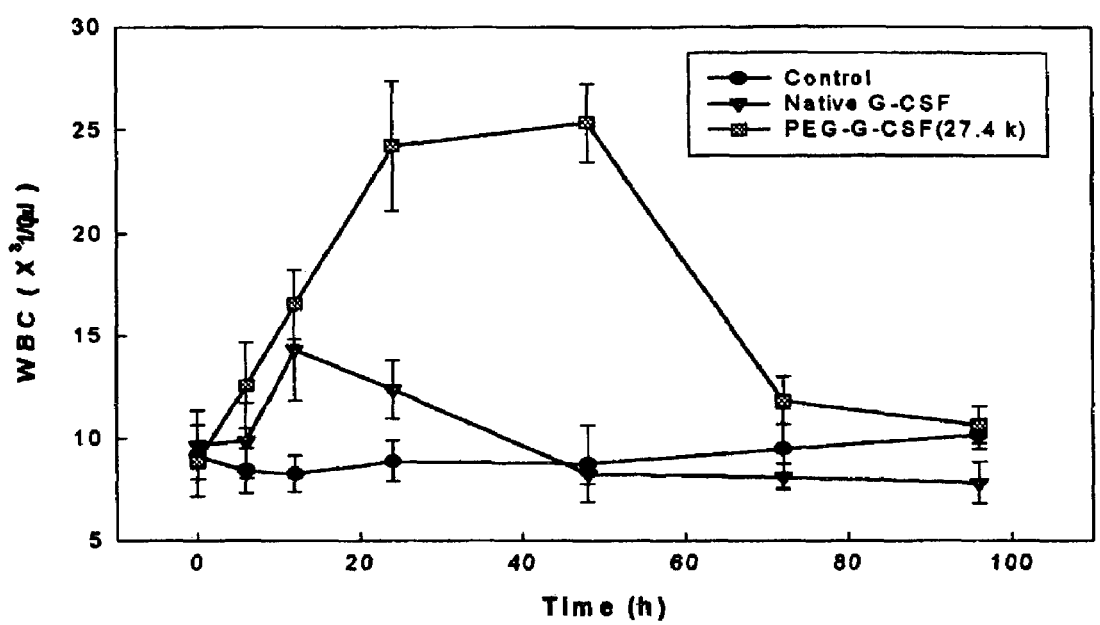
FIG. 2 shows the efficacy of biologically active conjugate (mPEG12000-OCH$_2$COGly-Gly)$_2$(2,4-diaminobutyric acid)-PEG'-G-CSF in rats.

Determination of White Blood Cell (WBC) count for (mPEG12000-OCH₂COGly-Gly)₂(2,4-diaminobutyric acid)-PEG'-G-CSF in rats 7-week old Sprague-Dawley rats weighing 220–240 g were purchased from Charles River Co. (Atsugi, Japan). 100 ug/kg of PEG-G-CSF of <Example 17> was injected to tail veins of rats. Native G-CSF was used for comparison as well as saline solution served as a control. Blood samples were withdrawn at time intervals of 0, 6, 12, 24, 48, 72, 96 hrs post injection through the tail vein. WBC count was measured by Automated Hematology Analyzer (Cysmex K-4500) shown in FIG. 2.

The present invention relates to highly reactive multi-armed hydrophilic polymer derivatives with a peptide spacer which provides balance between hydrophobicity and hydrophilicity derived from peptide spacer and polyethylene glycol, which increase the cell trafficking, endosomal disruption, the circulation half-life in blood, and the stability of conjugated protein, anti-sense oligonucleotide or plasmid DNA when conjugated thereto.

What is claimed is:

1. A biologically active conjugate of the following formula:

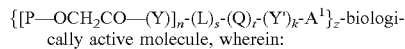
biologically active molecule, wherein:

P and Q may be the same or different and independently represent a biocompatible polymer;

t is an integer of 0 or 1;

Y and Y' may be the same or different and independently represent a peptide consisting of from 2 to 18 amino acid residues;

k is an integer of 0 or 1;

L represents aliphatic linking moiety or diaminocarboxylic acid;

s is an integer of 0 or 1;

n is an integer of 1 or 2;

$A^1$ is a linker between a biocompatible polymer and a biologically active molecule which comprises a functional group selected from the group consisting of —NHS, —NHNH2, carbonyl imidazole, nitrophenyl, isocyanate, sulfonyl chloride, aldehyde, glyoxal, epoxide, carbonate, cyanuric halide, dithiocarbonate, tosylate and maleimide;

and z is an integer of 1 or more as the number of polymers attached to the biologically active molecule, and wherein the conjugate is stable whereby the half-life of the biologically active molecule in the conjugate extends in vivo.

2. The conjugate according to claim 1 wherein the biologically active molecule is selected from the group consisting of proteins, peptides, polypeptides, enzymes, drugs, and small organic molecules.

3. The conjugate according to claim 2 wherein the protein or peptide is selected from the group consisting of alpha-, beta-, gamma-interferon, asparaginase, arginase, arginine deiminase, adenosine deaminase, superoxide dismutase, endotoxinase, catalase, chymotrypsin, lipase, uricase, adenosine diphosphatase, tyrosinase, glucose oxidase, glucosidase, galactosidase, glucouronidase, hemoglobin, blood factors (VII, VIII and IX), immunoglobins, cytokines such as interleukins, G-CSF, GM-CSF, PDGF, lectins, ricins, TNF, TGF, epidermal growth factor, human growth hormone, calcitonin, PTH, insulin, enkephalin, GHRP, LHRH and derivatives, calcitonin gene related peptide, thyroid stimulating hormone and thymic humoral factor.

4. A conjugate formed by non-covalently binding the biocompatible polymer as claimed in claim 1 and an anti-sense oligonucleotide, a gene or a plasmid DNA.

5. A pharmaceutical composition comprising a pharmaceutically acceptable amount of the conjugate as claimed in claim 1 and a pharmaceutically acceptable carrier.

6. The biologically active conjugate according to claim 1, wherein:

P and Q are polyethylene glycol;

t is 0;

Y and Y' are His-His;

k is 0;

L is lysine;

s is 1;

A is $NHNH_2$;

n is 2;

$A^1$ is —NH=NH—;

z is 1;

and the biologically active molecule is interferon.

7. The biologically active conjugate of claim 1, wherein the biologically active molecule is interferon.

* * * * *